United States Patent [19]

Uenishi et al.

[11] Patent Number: 5,089,373
[45] Date of Patent: Feb. 18, 1992

[54] POSITIVE PHOTORESIST COMPOSITION UTILIZING O-QUINONEDIAZIDE AND NOVOLAK RESIN

[75] Inventors: Kazuya Uenishi; Yasumasa Kawabe; Tadayoshi Kokubo, all of Shizuoka, Japan

[73] Assignee: Fuji Photo Film Co., Ltd., Kanagawa, Japan

[21] Appl. No.: 363,568

[22] Filed: Jun. 7, 1989

[30] Foreign Application Priority Data

Jun. 7, 1988 [JP] Japan ................................. 63-139904

[51] Int. Cl.$^5$ ........................ G03C 1/61; G03F 7/023; G03F 7/022
[52] U.S. Cl. ..................................... 430/191; 430/165; 430/192; 430/193
[58] Field of Search ................ 430/193, 192, 165, 191

[56] References Cited

U.S. PATENT DOCUMENTS 3,188,210  6/1965  Fritz et al. ........................... 430/193
4,407,926  10/1983  Stahlhofen ............................ 430/193

FOREIGN PATENT DOCUMENTS 60-121445  6/1985  Japan ..................................... 430/193

*Primary Examiner*—Charles L. Bowers, Jr.
*Assistant Examiner*—Christopher G. Young
*Attorney, Agent, or Firm*—Sughrue, Mion, Zinn, Macpeak & Seas

[57] ABSTRACT

A positive photoresist composition containing the combination of at least one alkali-soluble novolak resin and at least one light-sensitive compound represented by formula (I):

(I)

wherein each of $R_1$ to $R_{10}$, which may be the same or different, represents hydrogen, —OH, a substituted or unsubstituted alkyl group, a substituted or unsubstituted alkoxy group, a substituted or unsubstituted aryl group, a substituted or unsubstituted aralkyl group, a substituted or unsubstituted alkylester group, a substituted or unsubstituted arylester group, a substituted or unsubstituted aralkylester group, a substituted or unsubstituted alkylsulfonylester group, a substituted or unsubstituted arylsulfonylester group, provided that at least one of $R_1$ to $R_{10}$ represents $$-CR_{17},$$

where $R_{17}$ represents a substituted or unsubstituted alkyl group, a substituted or unsubstituted aryl group or a substituted or unsubstituted aralkyl group; and at least two of $R_1$ to $R_{10}$ represent and $R_{11}$ and $R_{12}$, which may be the same or different, each represents hydrogen, —OH, —COOH, —CN, a halogen atom, a substituted or unsubstituted alkyl group, a substituted or unsubstituted alkoxy group, a substituted or unsubstituted aralkyl group, —COOR$_{13}$, —R$_{14}$—COOH, or —R$_{15}$—COOR$_{16}$; where R$_{13}$ and R$_{16}$, which may be the same or different, each represents a substituted or unsubstituted alkyl group, a substituted or unsubstituted aryl group, or a substituted or unsubstituted aralkyl group; and R$_{14}$ and R$_{15}$ each represents a substituted or unsubstituted alkylene group, or a substituted or unsubstituted arylene group; provided that at least one of R$_{11}$ and R$_{12}$ represents a group other than hydrogen.

The positive photoresist composition has high resolving power and sensitivity, and a nearly perpendicular cross-section.

9 Claims, No Drawings

POSITIVE PHOTORESIST COMPOSITION UTILIZING O-QUINONEDIAZIDE AND NOVOLAK RESIN

FIELD OF THE INVENTION

This invention relates to a radiation-sensitive positive photoresist, and in particular it relates to photoresist compositions for fine working which have high resolving power and sensitivity and a cross-sectional form of a desirable pattern. Typical fields of application include the production of semiconductors such as integrated circuits, the production of circuit boards for liquid crystals and thermal heads and other such photofabrication processes.

BACKGROUND OF THE INVENTION

In general, compositions containing alkali-soluble resins and, as the photosensitive material, naphthoquinonediazido compounds are used as positive photoresist compositions. For example, "novolak phenol resin/naphthoquinone-diazide-substituted compounds" are disclosed in U.S. Pat. Nos. 3,666,473, 4,115,128 and 4,173,470 and, as a more typical composition, an example of a "novolak resin/trihydroxybenzophenone-1,1-naphthoquinonediazidosulfonic acid ester formed from cresol formaldehyde" is disclosed in "Introduction to Microlithography" by L. F. Thompson (ACS Publishing, No. 219, pp 112–121).

The novolak resin which is used as the binder is able to dissolve in aqueous alkaline solutions without swelling and has a particularly high resistance to plasma etching when used as a mask for etching the image formed, and it is therefore particularly useful in this application. Furthermore, although the naphthoquinonediazido compounds used as the light-sensitive substances themselves act as dissolution inhibitors by reducing the alkaline solubility of the novolak resin, they are distinctive in that they produce alkali-soluble materials when degraded upon irradiation by light and in fact work to raise the alkali solubility of the novolak resin and, due to this major property change in light, they are particularly useful as the light-sensitive substance in a positive photoresist.

Hitherto, numerous positive photoresists containing novolak resins and naphthoquinone diazide-based light-sensitive substances have been developed and produced on the basis of such considerations with adequate results for line working up to widths of about 1.5 to 2 μm.

However, the degree of integration of integrated circuits is ever increasing and it is becoming necessary to work extremely fine patterns, composed of lines with a width of less than 1 μm, in the manufacture of ultra-large scale integrated and other such semiconductor boards. In such applications, there is, in particular, a need for a photoresist having a high sensitivity in terms of high resolving power, high-precision pattern reproduction whereby the pattern of the exposed mask is copied accurately, and high producibility which, at present, the conventional positive photoresists mentioned above cannot satisfy.

SUMMARY OF THE INVENTION

The objects of this invention are to provide:
(1) a positive photoresist composition having a high resolving power,
(2) a positive photoresist composition in which the mask dimensions are accurately reproduced over a wide range of photomask line widths,
(3) a positive photoresist composition with which it is possible to produce a resist pattern of a cross-sectional form having a high aspect ratio in a pattern with line widths of 1 μm or less,
(4) a positive photoresist composition with which it is possible to produce a pattern in which the side walls of the pattern cross-section are in a form close to perpendicular,
(5) a positive photoresist composition having a wide development latitude, and
(6) a positive photoresist composition in which the resist image obtained is outstanding in its heat resistance, particularly in the production of semiconductor devices.

As a result of extensive studies the inventors have discovered that these and other objects of the present invention are attained by a positive photoresist composition cotaining the combination of at least one alkali-soluble novolak resin and at least one light-sensitive compound represented by formula [I]:

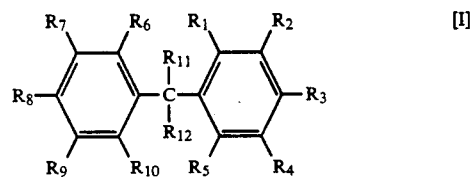

wherein each of $R_1$ to $R_{10}$, which may be the same or different, represents hydrogen, —OH, a substituted or unsubstituted alkyl group, a substituted or unsubstituted alkoxy group, a substituted or unsubstituted aryl group, a substituted or unsubstituted aralkyl group, a substituted or unsubstituted alkylester group, a substituted or unsubstituted arylester group, a substituted or unsubstituted aralkylester group, a substituted or unsubstituted alkylsulfonylester group, a substituted or unsubstituted arylsulfonylester group,

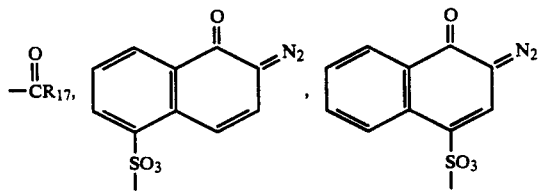

provided that at least one of $R_1$ and $R_{10}$ represent

where $R_{17}$ represents a substituted or unsubstituted alkyl group, a substituted or unsubstituted aryl group, or a substituted or unsubstituted aralkyl group; and at least two of $R_1$ to $R_{10}$ represent

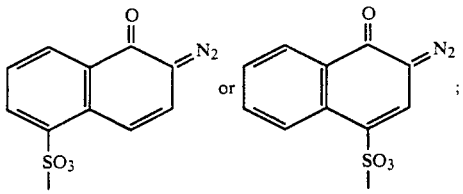

or

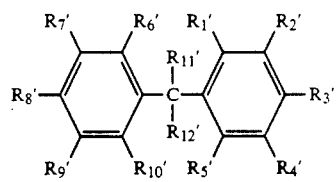

and $R_{11}$ and $R_{12}$, which may be the same or different, each represents hydrogen, —OH, —COOH, —CN, a halogen atom, a unsubstituted alkyl group, a substituted or unsubstituted alkoxy group, a substituted or unsubstituted aralkyl group, —COOR$_{13}$, —R$_{14}$—COOH, or —R$_{15}$—COOR$_{16}$, where R$_{13}$ and R$_{16}$, which may be the same or different, each represents a substituted or unsubstituted alkyl group, a substituted or unsubstituted aryl group, or a substituted or unsubstituted aralkyl group; and R$_{14}$ and R$_{15}$ each represents a substituted or unsubstituted alkylene group, or a substituted or unsubstituted arylene group; provided that at least one of R$_{11}$ and R$_{12}$ represents a group other than hydrogen.

DETAILED DESCRIPTION OF THE INVENTION

This invention is explained in further detail below. $R_1$ to $R_{13}$, $R_{16}$ and $R_{17}$ are preferably alkyl or alkoxy groups with 1 to 8 carbon atoms, aryl or aralkyl groups with 6 to 15 carbon atoms, alkyl or alkoxy groups with 1 to 8 carbon atoms substituted with alkoxy, aryloxy, aryl, hydroxyl, carboxyl, sulfonic acid, amino, nitro, silyl, silyl ether, cyano, aldehyde or mercapto groups or halogen atoms; or aryl or aralkyl groups with 6 to 15 carbon atoms substituted with alkoxy, aryloxy, aryl, hydroxyl, carboxyl, sulfonic acid, amino, nitro, silyl, silyl ether, cyano, aldehyde or mercapto groups or halogen atoms.

More preferable groups for $R_1$ to $R_{13}$, $R_{16}$ and $R_{17}$ include alkyl or alkoxy groups with 1 to 5 carbon atoms, aryl or aralkyl groups with 6 to 12 carbon atoms, alkyl or alkoxy groups with 1 to 5 carbon atoms substituted with alkoxy, hydroxyl, carboxyl, sulfonic acid, amino or silyl ether groups, or aryl or aralkyl groups with 6 to 12 carbon atoms substituted with alkoxy, hydroxyl, carboxyl, sulfonic acid, amino or silyl ether.

Furthermore, $R_{14}$ and $R_{15}$ are preferably alkylene groups with 1 to 8 carbon atoms, arylene groups with 6 to 15 carbon atoms, alkylene groups with 1 to 8 carbon atoms substituted with alkoxy, aryloxy, aryl, hydroxyl, carboxyl, sulfonic acid, amino, nitro, silyl, silyl ether, cyano, aldehyde or mercapto groups or halogen atoms, and arylene groups with 6 to 15 carbon atoms substituted with alkoxy, aryloxy, aryl, hydroxyl, carboxyl, sulfonic acid, amino, nitro, silyl, silyl ether, cyano, aldehyde or mercapto groups or halogen atoms.

The light-sensitive compound represented by general formula [I] can be obtained by reacting 1,2-naphthoquinonediazido-5(and/or-4)-sulfonyl chloride with the polyhydroxy compound represented by general formula [I']

[I']

Wherein each of R'$_1$ to R'$_{10}$, which may be the same or different, represents hydrogen, —OH, a substituted or unsubstituted alkyl group, a substituted or unsubstituted alkoxy group, a substituted or unsubstituted aryl group, a substituted or unsubstituted aralkyl group, a substituted or unsubstituted alkylester group, a substituted or unsubstituted arylester group, a substituted or unsubstituted aralkylester group, a substituted or unsubstituted alkylsulfonylester group, a substituted or unsubstituted arylsulfonylester group, $$-\overset{O}{\underset{\|}{C}}R_{17'},$$

provided that at least one of R'$_1$ to R'$_{10}$ represents:

$$-\overset{O}{\underset{\|}{C}}R_{17'},$$

where R'$_{17}$ represents a substituted or unsubstituted alkyl group, a substituted or unsubstituted aryl group, or a substituted or unsubstituted aralkyl group; and at least two of R'$_1$ to R'$_{10}$ represent —OH group; and R'$_{11}$ and R'$_{12}$, which may be the same or different, each represents hydrogen, —OH, —COOH, —CH, a halogen atom, a substituted or unsubstituted alkyl group, a substituted or unsubstituted alkoxy group, or a substituted or unsubstituted aralkyl group, —COOR'$_{13}$, —R'$_{14}$—COOH, or —R'$_{15}$—COOR'$_{16}$, where R'$_{13}$ and R'$_{16}$, which may be the same or different, each represents a substituted or unsubstituted alkyl group, a substituted or unsubstituted aryl group, a substituted or unsubstituted aralkyl group; and R$_{14}$ and R$_{15}$ each represents a substituted or unsubstituted alkylene group, or a substituted or unsubstituted arylene group; provided that at least one of R$_{11}$ and R$_{12}$ represents a group other than hydrogen.

Here, R'$_1$ to R'$_{13}$, R'$_{16}$ and R'$_{17}$ respectively represent the groups mentioned above, although they are preferably alkyl groups or alkoxy groups with 1 to 8 carbon atoms, aryl groups or aralkyl groups with 6 to 15 carbon atoms, alkyl groups or alkoxy groups with 1 to 8 carbon atoms substituted with alkoxy, aryloxy, aryl, hydroxyl, carboxyl, sulfonic acid, amino nitro, silyl, silyl ether, cyano, aldehyde or mercapto groups or halogen atoms and the like, or aryl groups or aralkyl groups with 6 to 15 carbon atoms substituted alkoxy, aryloxy, aryl, hydroxyl, carboxyl, sulfonic acid, amino, nitro, silyl, silyl ether, cyano, aldehyde or mercapto groups or halogen atoms and the like; and R'$_{14}$ and R'$_{15}$ are preferably alkylene groups with 1 to 8 carbon atoms, arylene groups with 6 to 15 carbon atoms, alkylene groups with 1 to 8 carbon atoms substituted with alkoxy, aryloxy, aryl, hydroxyl, carboxyl, sulfonic acid, amino, nitro, silyl, silyl ether, cyano, aldehyde or mercapto groups or halogen atoms and the like, or alkylene groups with 1 to 8 carbon atoms substituted with alkoxy, aryloxy, aryl, hydroxyl, carboxyl, sulfonic acid, amino, nitro, silyl, silyl ether, cyano, aldehyde or mercapto groups or halogen atoms and the like.

The compounds represented by general formula [I'] can be obtained by condensing a substituted or unsubstituted aldehyde and a phenol following the method of J. E. Driver et al. [J. Chem. Soc., 1954, pp 985–989], or alternatively by the Grignard reaction of S. S. Glen et al. [J. Chem. Soc., D 1970, (21), 1428–9] and the reduction reaction of De Vries et al. [Synthesis 1977, (4), 246–7]. The esterification reaction of the polyhydroxy compound represented by general formula [I'] and the 1,2-naphthoquiononediazido-5-sulfonyl chloride or 1,2-naphthoquinonediazido-4-sulfonyl chloride makes use of any conventional method. In other words, the desired amount of the polyhydroxy compound represented by formula [I'] and the 1,2-naphthoquinonediazido-5-sulfonyl chloride or 1,2-naphthoquinonediazido 4-sulfonyl chloride and a solvent such as dioxane, acetone, methyl ethyl ketone or N-methylpyrrolidone are placed in a flask, and condensation is carried out with the dropwise addition of a basic catalyst such as, for example, sodium hydroxide, sodium carbonate, sodium hydrogen carbonate or triethylamine. The product obtained is washed and then purified and dried. The light-sensitive substance represented by general formula [I] can be prepared using the above method.

A mixture of compound in which the esterification number and the esterification positions differ variously is obtained from the esterification reaction mentioned above. Accordingly, the "esterification rate" as referred to in this invention is defined as the average value of this mixture. The esterification rate is preferably in a range of 40 to 100% and more preferably 50 to 95%.

The esterification rate so defined can be controlled by the mixing ratios of the source materials, namely the compound [I'] and the 1,2 -naphthoquinonediazido-5(and/or-4)-sulfonyl chloride. In other words, in order to obtain a mixture with the desired esterification rate, it is sufficient to adjust the molar ratio of the source materials since the 1,2-naphthoquinonediazide-5(and/or-4)-sulfonyl chloride which is added essentially instigates the whole of the esterification reaction.

The alkali-soluble novolak resin which is used in this invention is obtained by the addition condensation of 0.6 to 1.0 mole of aldehyde to 1 mole of phenol in the presence of an acidic catalyst. For the phenol, it is possible to use phenol, o-cresol, m-cresol, p-cresol xylenol or the like, either singly or in a combination of 2 or more. Furthermore, as the aldehyde, it is possible to use formaldehyde, paraformaldehyde, furfural and the like, and, as the acidic catalyst, it is possible to use hydrochloric acid, sulfuric acid, formic acid, oxalic acid, acetic acid and the like. The novolak resin with a molecular weight of 1,000 to 50,000 obtained in this way exhibits alkali solubility.

The ratio in which the light-sensitive substance and the alkali soluble novolak resin are used in this invention is 5 to 100 parts by weight, and preferably 10 to 50 parts by weight of light-sensitive compound (1) to 100 parts by weight of novolak resin. At a use ratio of less than 5 parts by weight, the residual film rate is markedly reduced, and in excess of 100 parts by weight, the sensitivity and the solubility in the solvent are reduced.

The light-sensitive compounds represented by formula (I) are principally used in this invention although, where required, it is possible to use them in combination with esters of 1,2-naphtho-quinonediazido-5(and/or-4)-sulfonyl chloride with, for example, 2,3,4-trihydroxybenzophenone, 2,4,4'-trihydroxybenzophenone, 2,4,6-trihydroxybenzophenone and other such common light-sensitive substances. In such cases, it is possible to employ proportions of 100 parts by weight or less, and preferably 30 parts by weight or less, to 100 parts by weight of the light-sensitive compound represented by formula (1).

Polyhydroxy compounds can also be included in this invention in order to accelerate dissolution in the developing solution. Phenols, resorcinol, phloroglucinol, 2,3,4-trihydroxybenzophenone, 2,3,4,4'-tetrahydroxybenzophenone, 2,3,4,3',4',5'-hexahydroxybenzophenone, and acetone-pyrogallol condensation resins are included among preferred polyhydroxy compounds.

Solvents for dissolving the light-sensitive substance and the alkali soluble novolak resin of this invention, include, ketones (for example, methyl ethyl ketone, cyclohexanone), alcohol ethers (for example, ethylene glycol monomethyl ether, ethylene glycol monoethyl ether), ethers (for example, dioxane, ethylene glycol dimethyl ether), cellosolve esters (for example, methyl cellosolve acetate, ethyl cellosolve acetate), fatty acid esters (for example, methyl lactate, ethyl lactate, butyl acetate), hydrocarbon halides (for example, 1,1,2-trichloroethylene), and highly polar solvents (for example, dimethylacetamide, N-methylpyrrolidone, dimethylformamide, dimethylsulfoxide). These solvents can be used either singly or by mixing a number of solvents.

Dyes, plasticizers, auxiliary adhesives, surfactants and the like can be included in the positive photoresist composition of this invention. Specific examples, include dyes such as methyl violet, crystal violet and malachite green; plasticizers such as stearic acid, acetal resins, phenoxy resins and alkyd resins; auxiliary adhesives such as hexamethyldisilazane and chloromethylsilane; and a surfactants such as nonylphenoxypoly(ethyleneoxy)ethanol and octylphenoxypoly(ethyleneoxy)ethanol.

The positive photoresist of this invention is coated onto a semiconductor wafer or onto a glass, ceramic, metal or other such base to a thickness of 0.5 to 3 μm using a spin-coating method or a roller-coating method. After this, the positive image is obtained by heating, drying, baking in a circuit pattern or the like via an exposure mask using, for example, ultraviolet irradiation and developing. It is also possible to work a pattern into the substrate by etching using this positive image as a mask.

After coating the above positive photoresist composition onto a base such as is used in the manufacture of precision integrated circuit elements (for example, a silicon/silicon dioxide covering) using an appropriate coating method such as spinning or coating, it is possible to obtain a good resist by exposing it though by any method, such as any desirable mask and developing.

As the developing solution for the positive photoresist compositions of this invention, it is possible to use aqueous solutions of alkalies such as inorganic alkalies (for example, sodium hydroxide, potassium hydroxide, sodium carbonate, sodium silicate, sodium metasilicate, ammonia water), primary amines (for example, ethylamine, n-propyamine) secondary amines (for example, diethylamine, di-n-butylamine), tertiary amines (for example, triethylamine, methyldiethylamine), amino alcohols (for example, dimethylethanoelamine, triethanolamine), quaternary ammonium salts (for example, tetramethylammonium hydroxide, tetraethylammonium hydroxide) and cyclic amines (for example, pyrrole, piperidine). Furthermore, appropriate amounts of alcohols and surfactants can be added to the above aqueous alkali solutions.

The positive photoresist of this invention is outstanding in its high resolving power, faithful reproducibility, cross-sectional form of the resist image, development latitude, thermal resistance and the storage stability of the resist.

EXAMPLES

The present invention is illustrated in greater detail with reference to the following specific examples and embodiments but the present invention is not to be construed as being limited thereto. Unless otherwise indicated, all parts, percents and ratios are by weight.

EXAMPLES (1) TO (6), COMPARATIVE EXAMPLES (7) TO (9)

(1) Synthesis of light-sensitive substance (a)

10 g of 1,1-(5,5'-diacetyl-2,3,4,2',3',4'-hexahydroxy)-diphenylethane, 29.7 g of 1,2-naphthoquinonediazido-5-sulfonyl chloride and 300 ml of acetone were placed in a 3-neck flask and dissolved uniformly. Following this, an 11.7 g/40 ml mixture of triethylamine/acetone was slowly added dropwise and a reaction was carried out for 3 hours at 25° C. The reaction mixture was poured into 1,500 ml of a 1% aqueous hydrochloric acid solution, the precipitate which formed was filtered, washed and dried (40° C.) and 32.5 g of the 1,2-naphthoquinonediazido-5-sulfonate of 1,1-(5,5'-diacetyl-2,3,4,2',3',4'-hexahydroxy)diphenylethane were obtained

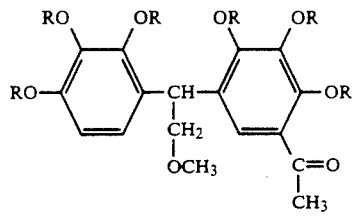

(2) Synthesis of light-sensitive substance (b)

10 g of 1,1-(5-acetyl-2,3,4,2',3',4'-hexahydroxy)diphenyl-2-methoxyethane, 30.8 g of 1,2-naphthoquinonediazido-5-sulfonyl chloride and 300 ml of acetone were placed in a 3-neck flask and mixed uniformly. Following this, a 12.1 g/40 ml mixture of triethylamine/acetone was slowly added dropwise and a reaction was carried out for 3 hours at 25° C. The reaction mixture was poured into 1,500 ml of a 1% aqueous hydrochloric acid solution, the precipitate which formed was filtered, washed and dried (40° C.) and 33.0 g of the 1,2-naphthoquinonediazido-5-sulfonate of 1,1-(5-acetyl-2,3,4,2',3',4'-hexahydroxy)diphenyl-2-methoxyethane were obtained.

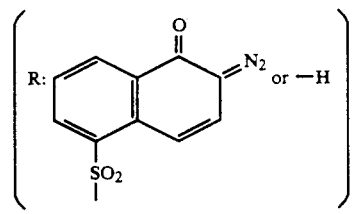

(3) Synthesis of light-sensitive substance (c)

10 g of methyl 1,1-(5,3'-diacetyl-2,3,4,4',5',6'-hexahydroxy)diphenylacetate, 31.1 g of 1,2-naphthoquinonediazido-5-sulfonyl chloride and 300 ml of acetone were placed in a 3-neck flask and dissolved uniformly. Following this, a 12.3 g/40 ml mixture of triethylamine/acetone was slowly added dropwise and a reaction was carried out for 3 hours at 25° C. The reaction mixture was poured into 1,500 ml of a 1% hydrochloric acid solution, the precipitate which was formed was filtered, washed and dried (40° C.) and 34.9 g of the 1,2-naphthoquinonediazido-5-sulfonate of methyl 1,1-(5,3'-diacetyl-2,3,4,4',5',6'-hexahydroxy)-diphenylacetate were obtained.

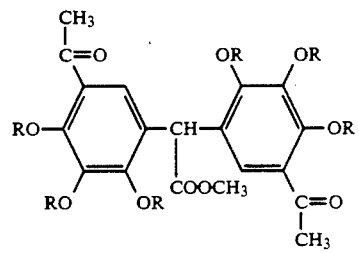

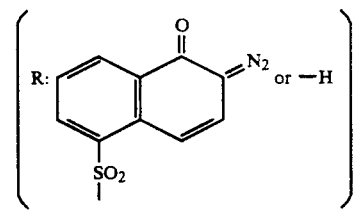

(4) Synthesis of light-sensitive substance (d)

10 g of 1,1-(5-acetyl-2,3,4,2',4',6'-hexahydroxy)-diphenyl-2-hydroxyethane, 40 g of 1,2-naphthoquinonediazido-5-sulfonyl chloride and 350 ml of acetone were placed in a 3-neck flask and dissolved uniformly. Following this, a 15.8 g/50 ml mixture of triethylamine/acetone was slowly added dropwise and a reaction was carried out for 3 hours at 25° C. The reaction mixture was poured into 1,700 ml of a 1% aqueous hydrochloric acid solution, the precipitate which was formed was filtered, washed and dried (40° C.) and 41 g of the 1,2-naphthoquinonediazido-5-sulfonate of 1,1-(5-acetyl- 2,3,4,2',4',6'-hexahydroxy)diphenyl-2-hydroxyethane were obtained.

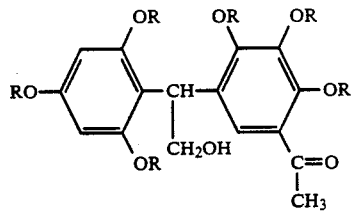

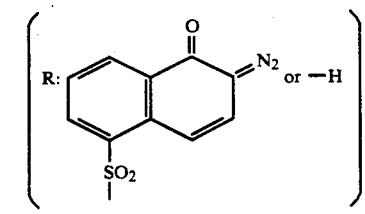

(5) Synthesis of light-sensitive substance (e)

10 g of 1,1-(2,4,6,2',4'-pentahydroxy-3-propanooyl)-diphenylethanol, 36.2 g of 1,2-naphthoquinonediazido-5-sulfonyl chloride and 300 ml of acetone were placed in a 3-neck flask and dissolved uniformly. Following this, a 10.4 g/40 ml mixture of triethylamine/acetone was slowly added dropwise and a reaction was carried out for 3 hours at 25° C. The reaction mixture was poured into 1,500 ml of a 1% aqueous hydrochloric acid solution, the precipitate which was formed was filtered, washed and dried (40° C.) and 38.3 g of the 1,2-naphthoquinonediazido-5-sulfonate of 1,1-(2,4,6,2', 4'-pentahydroxy-3-propanoyl)diphenylethanol were obtained.

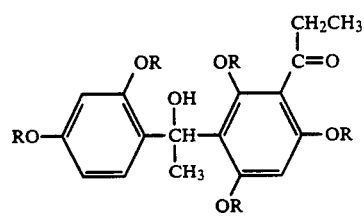

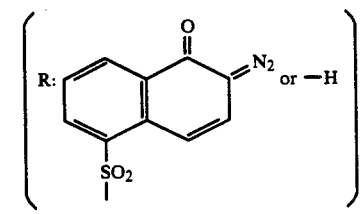

(6) Synthesis of light-sensitive substance (f)

10 g of 4-nitrophenyl 1,1-(5,5'-diacetyl-2,3,4,2',3',4'-hexahydroxy)acetate, 27.2 g of 1,2-naphthoquinonediazido-5-sulfonyl chloride and 300 ml of acetone were placed in a 3-neck flask and dissolved uniformly. Following this, a 10.8 g/40 ml mixture of triethylamine/acetone was slowly added dropwise and a reaction was carried out for 3 hours at 25° C. The reaction mixture was poured into 1,500 ml of a 1% aqueous hydrochloric acid solution, the precipitate which was formed was filtered, washed and dried (40° C.) and 32.0 g of the 1,2-naphthoquinonediazido-5-sulfonate of 4-nitrophenyl 1,1-(5,5'-diacetyl-2,3,4,2',3',4'-hexahydroxy)acetate were obtained.

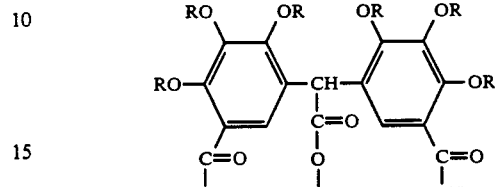

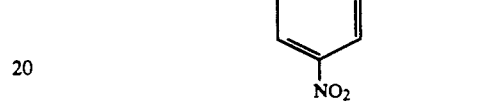

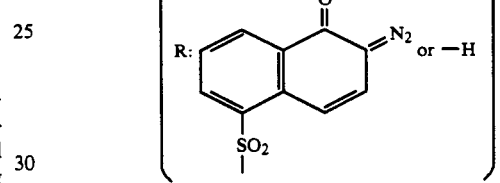

(7) Synthesis of light-sensitive substance (g)
(comparative example)

10 g of 2,3,4,4'-tetrahydroxybenzophenone, 30 g of 1,2-naphthoquinonediazido-5-sulfonyl chloride and 300 ml of acetone were placed in a 3-neck flask and dissolved uniformly. Following this, a 11.3 g/30 ml mixture of triethylamine/acetone was slowly added dropwise and a reaction was carried out for 3 hours at 25° C. The reaction mixture was poured into 1,500 ml of a 1% aqueous hydrochloric acid solution, the precipitate which was formed was filtered, washed and dried (40° C.) and 32.8 g of the 1,2-naphthoquinonediazido-5-sulfonate of 2,3,4,4'-tetrahydroxybenzophenone were obtained.

(8) Synthesis of light-sensitive substance (h)
(comparative example)

10 g of 5,5'diacetyl-2,3,4,2',3',4'-hexahydroxydiphenylmethane, 33 g of 1,2-naphthoquinonediazido-5-sulfonyl chloride and 300 ml of acetone were placed in a 3-neck flask and dissolved uniformly. Following this, a 13.1 g/40 ml mixture of triethylamine/acetone was slowly added dropwise and a reaction was carried out for 3 hours at 25° C. The reaction mixture was poured into 1,500 ml of a 1% aqueous hydrochloric acid solution, the precipitate which formed was filtered, washed and dried (40° C.) and 37.4 g of the 1,2-naphthoquinonediazido-5-sulfonate of 5,5'-diacetyl-2,3,4,2',3',4'-hexahydroxydiphenylmethane were obtained.

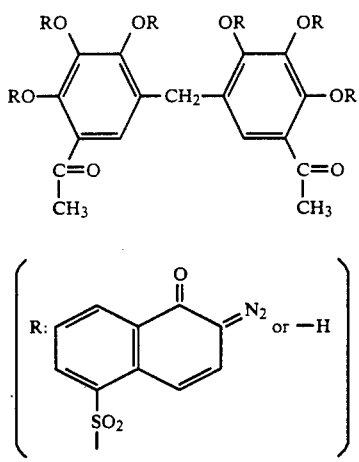

(9) Synthesis of light-sensitive substance (i) (comparative example)

10 g of 2,2-(2,3,4,2',3',4'-hexahydroxy)diphenylpropane, 43.2 g of 1,2-naphthoquinonediazo-5-sulfonyl chloride and 400 ml of acetone were placed in a 3-neck flask and dissolved uniformly. Following this, a 17.1 g/50 ml mixture of triethylamine/acetone was slowly added dropwise and a reaction was carried out for 3 hours at 25° C. The reaction mixture was poured into 2.000 ml of a 1% aqueous hydrochloric acid solution, the precipitate which was formed was filtered, washed and dried (40° C.) and 45.2 g of the 1,2-naphthoquinonediazido-5-sulfonate of 2,2-(2,3,4,2',3',4'-hexahydroxy)diphenylpropane were obtained.

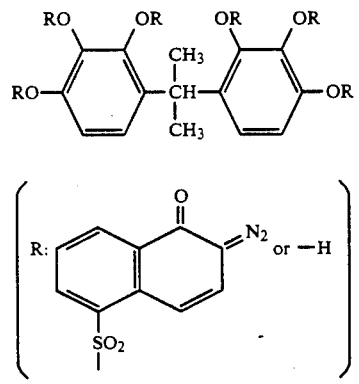

(10) Synthesis of the novolak resin 40 g of m-cresol, 60 g of p-cresol, 49.5 g of a 37% aqueous formalin solution and 0.05 g of oxalic acid were placed in a 3-neck flask and a reaction carried out for 7 hours raising the temperature of 100° C. while stirring. After the reaction, the product was cooled to room temperature and the pressure reduced to 30 mmHg. Following this, the temperature was gradually raised to 150° C. and the water and unreacted monomers were removed. The novolak resin obtained had an average molecular weight of 8,000 (polystyrene calculated).

(11) Preparation and evaluation of the positive photoresist composition

Photoresist compositions were obtained by dissolving 1.25 g respectively of the light-sensitive substances (a) to (i) shown in Table 1 which were obtained in (1) to (9) above and 5 g of the cresol novolak resin (molecular weight 8,000) obtained in (10) above in 15 g of ethyl cellosolve acetate and filtering using a 0.2 μm micro-filter. This photoresist was coated onto a silicon wafer using a spinner, and a resist film with a film thickness of 1.5 μm was obtained by drying for 30 minutes at 90° C. with a convection oven in a nitrogen atmosphere. After exposing this film using a reduced projection exposing apparatus (the NSR 1505G made by the Nikon Company) it was developed for 1 minute in an aqueous 2.38% tetramethylammonium hydroxide solution, washed for 30 seconds and dried. The resist pattern of the silicon wafer obtained in this way was examined under a scanning electron microscope and the resist was evaluated. The results are shown in Table 2.

The sensitivity was determined using the reciprocal of the exposure reproducing a 2.0 μm mask pattern and is shown as a relative value compared to the sensitivity of Comparative Example 1.

The residual film index is represented as a percentage of the ratio of the unexposed portion before and after development.

The resolving power represents the limiting resolving power at an exposure reproducing a mask pattern of 2.0 μm.

TABLE 1

| No. | Light-sensitive substance | Estrification (%) |
|---|---|---|
| Examples | | |
| 1 | a The 1,2-naphthoquinonediazido-5-sulfonate of 1,1-(5,5'-diacetyl-2,3,4,2',3',4'-hexahydroxy)diphenylethane | 67 |
| 2 | b The 1,2-naphthoquinonediazido-5-sulfonate of 1,1-(5-acetyl-2,3,4,2',3',4'-hexahydroxy)diphenyl-2-methoxyethane | 75 |
| 3 | c The 1,2-naphthoquinonediazido-5-sulfonate of methyl 1,1-(5,3'-diacetyl-2,3,4,4',5',6'-hexahydroxy)diphenylacetate | 78 |
| 4 | d The 1,2-naphthoquinonediazido-5-sulfonate of 1,1-(5-acetyl-2,3,4,2',4',6'-hexahydroxy)diphenyl-2-hydroxyethane | 83 |
| 5 | e The 1,2-naphthoquinonediazido-5-sulfonate of 1,1-(2,4,6,2',4'-pentahydroxy-3-propanoyl, diphenylethanol | 90 |
| 6 | f The 1,2-naphthoquinonediazido-5-sulfonate of 4-nitrophenyl 1,1-(5,5'-diacetyl-2,3,4,2',3',4'-hexyahydroxy)acetate | 87 |

TABLE 1-continued

| No. | Light-sensitive substance | Estrification (%) |
|---|---|---|
| Comparative Examples | | |
| 1 | g The 1,2-naphthoquinonediazido-5-sulfonate of 2,3,4,4'-tetrahydroxybenzophenone | 69 |
| 2 | h The 1,2-naphthoquinonediazido-5-sulfonate of 5,5'-diacetyl-2,3,4,2',3',4'-hexahydroxydiphenylmethane | 72 |
| 3 | i The 1,2-naphthoquinonediazido-5-sulfonate of 2,2-(2,3,4,2',3',4'-hexahydroxy)diphenylpropane | 78 |

TABLE 2

| Example | Light-sensitive Substance | Relative Sensitivity | Residual Film Index (%) | Resolving Power (μm) | Thermal Resistance (°C.) | Resist Form (θ) |
|---|---|---|---|---|---|---|
| Example | | | | | | |
| 1 | a | 1.5 | 100 | 0.6 | 150 | 87 |
| 2 | b | 1.4 | 100 | 0.6 | 150 | 89 |
| 3 | c | 1.2 | 99 | 0.7 | 160 | 88 |
| 4 | d | 1.3 | 99 | 0.7 | 150 | 87 |
| 5 | e | 1.4 | 100 | 0.6 | 150 | 88 |
| 6 | f | 1.1 | 100 | 0.7 | 160 | 86 |
| Comparative Example | | | | | | |
| 1 | g | 1.0 | 98 | 0.8 | 140 | 82 |
| 2 | h | 1.2 | 97 | 0.8 | 140 | 83 |
| 3 | i | 0.9 | 98 | 0.8 | 150 | 85 |

In the above Table 2, "thermal resistance" is denoted by a temperature so as not to cause pattern deformation when silicon wafer having resist pattern is baked in a convection oven for 30 minutes. "Resist form" is denoted by an angle (θ) which is made by a side wall of resist and a plane of silicon wafer in a cross-sectional form of 1.0 μm resist pattern.

As is apparent from the results, the resists using the light-sensitive substances (a) to (f) are excellent, especially in a resolving power and a resist form. Since the light-sensitive substances of the present invention are excellent in solubility in ethylcellosolve, the resist composition solution containing the light-sensitive substance did not cause precipitation even being allowed to stand for 30 days at 40° C. On the other hand, the resist composition solutions containing comparative light-sensitive substances (h) and (i) caused precipitation after storage under the same conditions.

While the invention has been described in detail and with reference to specific examples thereof, it will be apparent to one skilled in the art that various changes and modifications can be made therein without departing from the spirit and scope thereof.

What is claimed is:

1. A positive photoresist composition comprising in admixture at least one alkali-soluble novolak resin and at least one light-sensitive compound represented by formula (I):

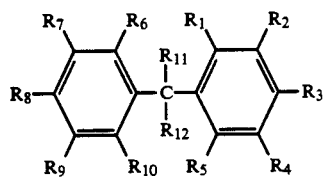

wherein each of $R_1$ to $R_{10}$, which may be the same or different, represents hydrogen, —OH, a substituted or unsubstituted alkyl group, a substituted or unsubstituted alkoxy group, a substituted or unsubstituted aryl group, a substituted or unsubstituted aralkyl group, a substituted or unsubstituted alkylester group, a substituted or unsubstituted arylester group, a substituted or unsubstituted aralkylester group, a substituted or unsubstituted alkylsulfonylester group, a substituted or unsubstituted arylsulfonylester group,

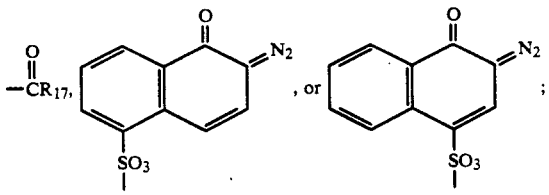

provided that at least one of $R_1$ to $R_{10}$ represents

where $R_{17}$ represents a substituted or unsubstituted alkyl group, a substituted or unsubstituted aryl group or a substituted or unsubstituted aralkyl group; and at least two of $R_1$ to $R_{10}$ represent

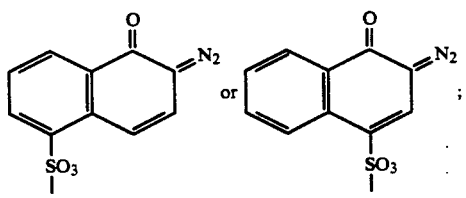

and $R_{11}$ and $R_{12}$, which may be the same or different, each represents hydrogen, —OH, —COOH, —CN, a halogen atom, a substituted or unsubstituted alkyl group, a substituted or unsubstituted alkoxy group, a substituted or unsubstituted aralkyl group, —COOR$_{13}$, —R$_{14}$—COOH, or —R$_{15}$—COOR$_{16}$; where $R_{13}$ and $R_{16}$, which may be the same or different, each represents a substituted or unsubstituted alkyl group, a substituted or unsubstituted aryl group, or a substituted or unsubstituted aralkyl group; and $R_{14}$ and $R_{15}$ each represents a substituted or unsubstituted alkylene group, or a substituted or unsubstituted arylene group; provided that at least one of $R_{11}$ represents a group other than hydrogen; wherein from 5 to 100 parts by weight of said light-sensitive compound represented by formula (I) are present per 100 parts by weight of said novolak resin.

2. The positive photoresist composition as claimed in claim 1, wherein at least two of $R_1$ to $R_{10}$ represent

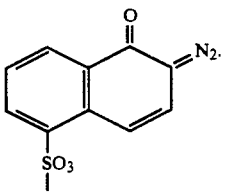

3. The positive photoresist composition as claimed in claim 1, wherein at least two of $R_1$ to $R_{10}$ represent

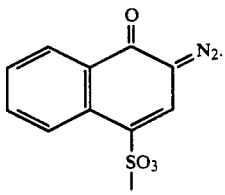

4. The positive photoresist composition as claimed in claim 1, wherein each of said alkyl groups and alkoxy groups represented by $R_1$ to $R_{13}$, $R_{16}$ and $R_{17}$ contains 1 to 8 carbon atoms; each of said aryl groups and aralkyl groups represented by $R_1$ to $R_{13}$, $R_{16}$ and $R_{17}$ contains 6 to 15 carbon atoms; each of said substituted alkyl groups and substituted alkoxy groups represented by $R_1$ to $R_{13}$, $R_{16}$ and $R_{17}$ is substituted with a substituent selected from an alkoxy group, an aryloxy group, an aryl group, a hydroxyl group, a carboxyl group, a sulfonic acid group, an amino group, a nitro group, a silyl group, a silyl ether group, a cyano group, an aldehyde group, a mercapto group or a halogen atom; and each of said substituted aryl groups and substituted aralkyl groups represented by $R_1$ to $R_{13}$, $R_{16}$ and $R_{17}$ is substituted with at least one substituent selected from an alkoxy group, an aryloxy group, an aryl group, a hydroxyl group, a carboxyl group, a sulfonic acid group, an aryl group, a nitro group, a silyl group, a silyl ether group, a cyano group, an aldehyde group, a mercapto group or halogen atoms.

5. The positive photoresist composition as claimed in claim 1, wherein each of $R_{14}$ and $R_{15}$ represents an alkylene group containing 1 to 8 carbon atoms; an arylene group containing 6 to 15 carbon atoms; an alkylene group containing 1 to 8 carbon atoms substituted with an alkoxy group, an aryloxy group, an aryl group, a hydroxyl group, a carboxyl group, a sulfonic acid group, an amino group, a nitro group, a silyl group, a silyl ether group, a cyano group, an aldehyde group, a mercapto group, or a halogen atom; or an arylene group containing 6 to 15 carbon atoms substituted with an alkoxy group, an aryloxy group, an aryl group, a hydroxyl group, a carboxyl group, a sulfonic acid group, an amino group, a nitro group, a silyl group, a silyl ether group, a cyano group, an aldehyde group, a mercapto group, or a halogen atom.

6. The positive photoresist composition as claimed in claim 1, comprising from 10 to 50 parts by weight of said light-sensitive compound represented by formula (I) per 100 parts by weight of said novolak resin.

7. The positive photoresist composition as claimed claim 6, further comprising up to 100 parts by weight of a second light-sensitive compound selected from an ester of 1,2-naphthoquinonediazido-5-sulfonyl chloride and an ester of 1,2-naphthoquinonediazido-4-sulfonyl chloride, with any of 2,3,4-trihydroxybenzophenone, 2,4,4'-trihydroxybenzophenone, and 2,4,6-trihydroxybenzophenone; per 100 parts by weight of said light-sensitive compound represented by formula (I).

8. The positive photoresist composition as claimed in claim 7, comprising at most 30 parts by weight of said second light-sensitive compound per 100 parts by weight of said light-sensitive compound represented by formula (I).

9. The positive photoresist composition as claimed in claim 7, further comprising a polyhydroxy compound.

* * * * *